United States Patent [19]

Riedel et al.

[11] 3,938,347
[45] Feb. 17, 1976

[54] LEVEL CONTROL APPARATUS AND METHOD FOR CRYOGENIC LIQUIDS

[75] Inventors: Hans J. Riedel, Petaluma; Vernon C. Spellman, Santa Rosa, both of Calif.

[73] Assignee: Optical Coating Laboratory, Inc., Santa Rosa, Calif.

[22] Filed: Apr. 12, 1974

[21] Appl. No.: 460,376

[52] U.S. Cl. .......................... 62/55; 62/49; 73/295; 137/392; 340/244 C
[51] Int. Cl.² ............................................. F17C 7/02
[58] Field of Search ............ 62/49, 55, 129; 73/295; 137/392; 340/244 C

[56] References Cited
UNITED STATES PATENTS

| | | | |
|---|---|---|---|
| 3,049,887 | 8/1962 | Sharp et al. | 62/55 |
| 3,130,561 | 4/1964 | Hnilicka, Jr. | 62/45 |
| 3,161,050 | 12/1964 | Exner | 73/295 |
| 3,205,665 | 9/1965 | Van Horn | 62/45 |
| 3,279,198 | 10/1966 | Ayers et al. | 62/45 |
| 3,280,627 | 10/1966 | Cousins et al. | 73/295 |
| 3,324,722 | 6/1967 | Reicks | 73/295 |
| 3,371,533 | 3/1968 | Dumas | 73/295 |
| 3,496,773 | 2/1970 | Cornish | 73/295 |
| 3,633,372 | 1/1972 | Kimmell et al. | 62/55 |

*Primary Examiner*—William F. O'Dea
*Assistant Examiner*—Ronald C. Capossela
*Attorney, Agent, or Firm*—Flehr, Hohbach, Test, Albritton & Herbert

[57] ABSTRACT

Level control apparatus for cyrogenic liquids having a cryogenic liquid. Means is provided for introducing cryogenic liquid into the chamber and outlet means is provided to permit removal of the cryogenic liquid from the chamber. Level sensing means is mounted on the flask and has a probe extending into the chamber so that it will come in contact with the cryogenic liquid when the cryogenic liquid reaches a predetermined level within the chamber. The probe includes a thermocouple with a resistor secured to the thermocouple for heating the thermocouple. When the resistor is in contact with the cryogenic liquid, the thermocouple remains cold and provides a signal of one type. When the resistor is uncovered by the cryogenic liquid and the thermocouple becomes hot, a signal of a different type is provided. The signals from the thermocouples are utilized for controlling the entrance of the cryogenic liquid into the chamber and to maintain the liquid level at a predetermined level within the chamber. Two thermocouples and two resistors are utilized for the probe means to greatly reduce the cycling required for operating the filling means for the chamber.

7 Claims, 3 Drawing Figures

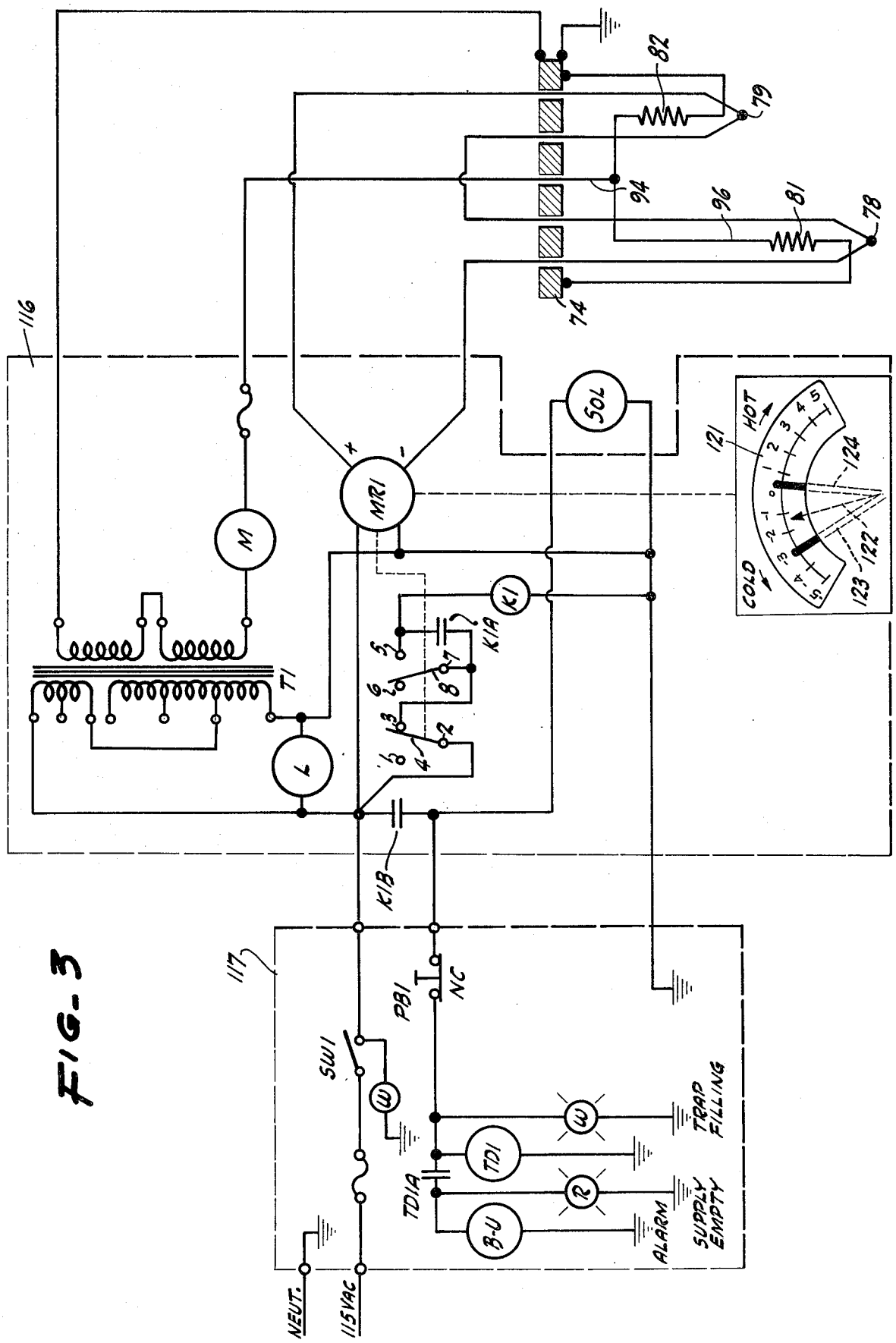

3,938,347

LEVEL CONTROL APPARATUS AND METHOD FOR CRYOGENIC LIQUIDS

BACKGROUND OF THE INVENTION

Level control apparatus has heretofore been provided for cryogenic liquids. However, many problems have been encountered with the same. Their action has been erratic causing much spillage and wastage of the cryogenic liquid. In addition, they have been relatively insensitive to liquid levels. They have also required a great deal of maintenance which has made it necessary to shut down the equipment with which they are utilized. There is, therefore, a need for a new and improved liquid level control apparatus and method for cryogenic liquids.

SUMMARY OF THE INVENTION AND OBJECTS

The level control apparatus for cryogenic liquid is comprised of an insulated flask having a chamber for holding a cryogenic liquid. Inlet means is mounted on the flask introducing the cryogenic liquid into the chamber. Outlet means is mounted on the flask to permit the cryogenic liquid to be removed from the flask. Level sensing means is mounted in the flask and has a probe extending into the chamber so that it comes in contact with the liquid when the liquid reaches a predetermined level in the chamber. The probe includes a thermocouple producing an output voltage of one polarity when it is at a temperature near that of cryogenic liquid and a voltage of opposite polarity when it is at a temperature which is substantially above that of the cryogenic liquid. The probe means also includes heating means connected to the thermocouple for heating the thermocouple. The heating means is adapted to come into contact with cryogenic liquid when it reaches the predetermined level. The signal from the thermocouple is utilized for controlling the flow of cryogenic liquid into the chamber so that the liquid level in the chamber is maintained above a predetermined level.

In general, it is an object of the present invention to provide a liquid level control system and method for cryogenic liquids which is very reliable.

Another object of the invention is to provide an apparatus and method of the above character which greatly reduces usage and waste of the cryogenic liquid.

Another object of the invention is to provide an apparatus of the above character which is relatively maintenance-free.

Another object of the invention is to provide an apparatus and method of the above character in which the cycle is readily controllable.

Another object of the invention is to provide an apparatus and method of the above character which is operable over long periods of time.

Another object of the invention is to provide an apparatus and method of the above character in which atmospheric air is prevented from entering the apparatus after it is placed in operation.

Additional objects and features of the invention will appear from the following description in which the preferred embodiment is set forth in detail in conjunction with the accompanying drawing.

BRIEF DESCRIPTION OF THE DRAWINGS

FIG. 3 is a circuit diagram of the level control apparatus in which certain of the parts are schematically illustrated.

DESCRIPTION OF PREFERRED EMBODIMENT

Figure 1:
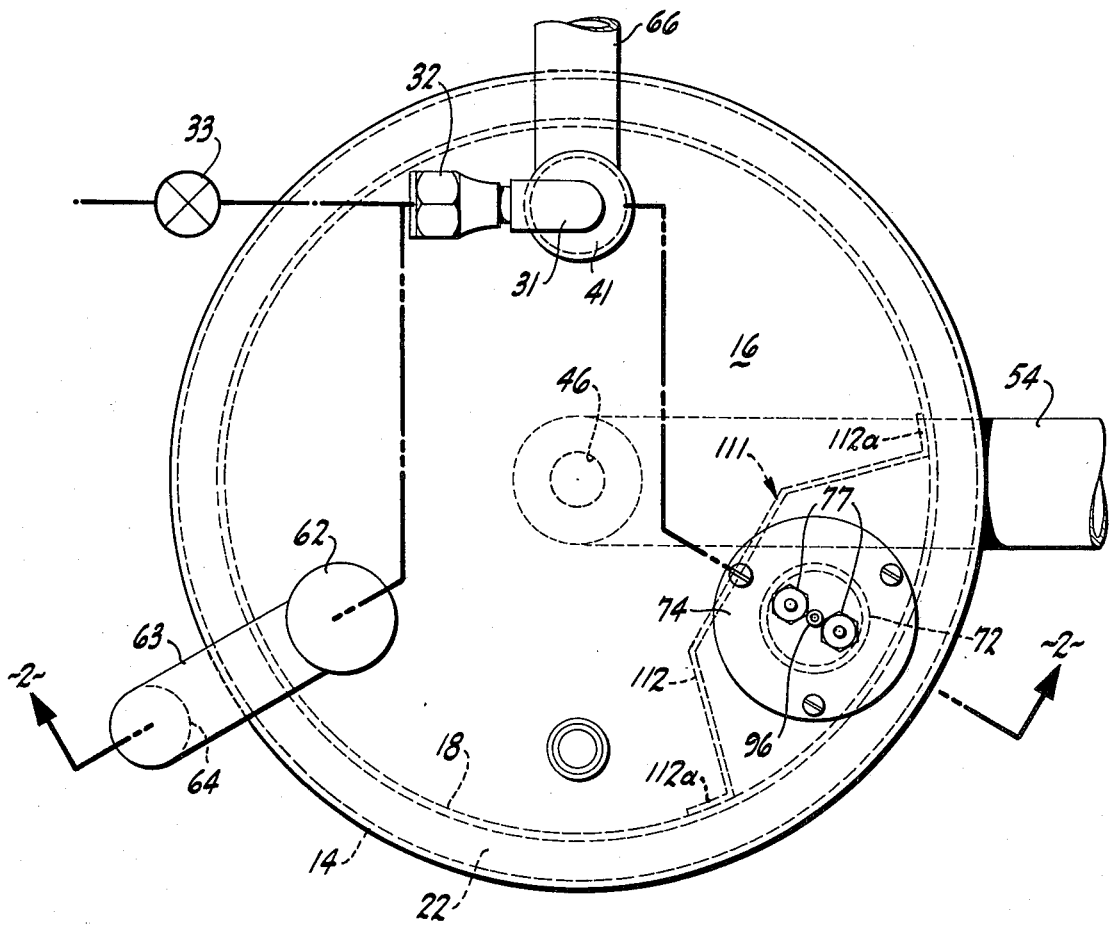
FIG. 1 is a top plan view of the Dewar flask forming a part of the level control apparatus incorporating the present invention.

The level control apparatus for cryogenic liquids for use with a vacuum chamber consists of a Dewar flask or vessel 11 which consists of first and second containers or cylinders 12 and 13 with the second container being disposed within the first container and having a size which is less than that of the first container. The outer or first container 12 is provided with a cylindrical side wall 14, planar top and bottom walls 16 and 17. Similarly, the inner or second container 13 is provided with a cylindrical side wall 18 and top and bottom walls 19 and 21. From the foregoing, it can be seen that the first and second containers 12 and 13 form first and second chambers 22 and 23 which are closed with the exit and entrance ports as hereinafter described. By way of example, the inner cylinder or container 13 can have a size such as 9 in. in diameter and 10 in. in height, whereas the first or outer container 12 can have a diameter of approximately 10 in. and a height of approximately 11 in., thus providing approximately ½ inch spacing between the side walls 14 and 18 and the top and bottom walls.

The space 22 between the containers 12 and 13 is evacuated after the fabrication of the Dewar flask or vessel 11 has been completed to a suitable vacuum ranging from approximately 10 to 1 microns. This is to provide insulation in a manner well known to those skilled in the art. Additional insulation is provided by placing two sheets of a metallic foil 26 of a suitable material such as aluminum in the space between the first and second containers as shown in the drawing. The aluminum foil 26 can have a thickness ranging from 0.003 to 0.005 of an inch. The aluminum foil preferably is wrinkled to minimize physical contact between surfaces.

Figure 2:
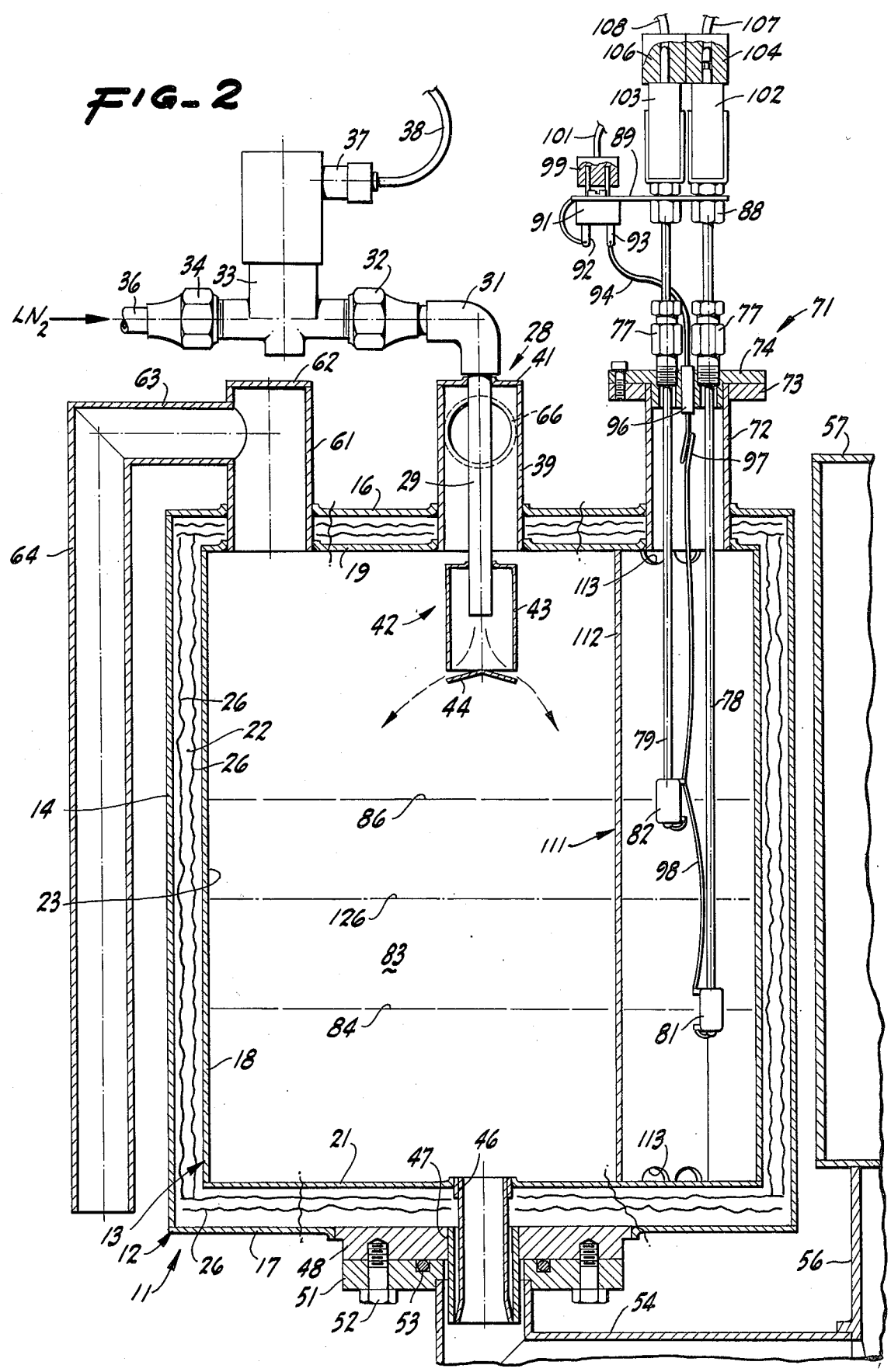
FIG. 2 is a cross-sectional view taken along the line 2—2 of FIG. 1.

Means is provided for introducing a cryogenic liquid, such as liquid nitrogen ($LN_2$) into the chamber 23, and consists of an inlet assembly 28 which is mounted in the top walls 16 and 19. The inlet assembly 28 consists of an inlet tube 29 which is connected to an elbow 31. The elbow 31 is connected to a fitting 32 which is threaded onto one end of an electrically operated solenoid valve 33. The other end of the valve 33 is connected to a fitting 34. The fitting 34 is connected to a line 36 which is insulated and which is connected either into a manifold or into a tank (not shown) which serves as the source for the cryogenic liquid. A electrical fitting 37 is connected to the solenoid operated valve 33 and is connected by a cable 38 to suitable electrical controls, hereinafter described. A sleeve 39 is concentric with the tube 29 and extends through the top walls 16 and 19 and is secured thereto by suitable means such as heliarc welding to provide a vacuum-tight seal. The sleeve 39 is open at its lower extremity and opens into the chamber 23. The upper end of the sleeve is provided with a cap 41 through which the tube 29 extends and into which it is sealed to provide a vacuum-tight seal. A diffuser assembly 42 is mounted on the lower extremity of the inlet tube 29 and consists of a cup-shaped cylinder 43 slightly smaller in size than the cylinder 39. The cup-shaped cylinder 43 is open at its bottom end and opens into the chamber 23. A circular diffuser plate 44 which is V-shaped in cross-section is secured to the lower extremity of the cylinder 43 by suitable means such as welding. As can be seen from FIG. 2, the V-shaped plate 44 has its apex secured to the lower extremities of the cylinder 43 and extends diametrically thereof. As also can be seen from FIG. 2, the sides of the plate are inclined downwardly away from the lower extremities of the cylinder 43 so that liquid nitrogen being introduced through the tube 29 diffuses outwardly in a circumferential fashion from the diffuser assembly 42 to provide a generally cone-shaped discharge from the diffuser assembly 42. It can be seen that the tube 29 and the diffuser assembly 42 are positioned in such a manner that the cryogenic liquid is discharged near the upper end of the chamber 23.

Means is provided for permitting the cryogenic liquid to flow by force of gravity from the Dewar flask 11 and consists of a tube 46 which serves as an inner bottom neck secured by suitable means such as welding to the bottom wall 21. The tubular member or neck 46 opens into the lower extremity of the chamber 23 as can be seen from FIG. 2. The lower extremity of the member or neck 46 is flanged outwardly and is secured to the lower extremity of an outer tube 47 which is secured to a flange 48 mounted on the bottom wall 17. As can be seen from FIG. 2, there is provided a concentric space 49 between the outer tube 47 and the inner tube 46 which is open to the space 22 and is thus evacuated as is the space 32. Another flange 51 is secured to the flange 48 by cap screws 52. O-ring means 53 is provided for establishing a vacuum-tight seal between the flanges 51 and 48. An elbow 54 is secured to the flange 51 and receives the lower extremity of the outer tube 47. The elbow 54 is connected into the trap of a vacuum pump 56 of a conventional type. The vacuum pump 56 is connected to a vacuum chamber 57 of a coating machine of a conventional type.

Vent pipe means is provided for venting the second chamber 13 to the atmosphere and consists of a cylindrical member or tube 61 which is mounted in the top walls 16 and 19 and opens into the upper extremity of the chamber 23 within the second container 13. The upper end of the cylindrical member 61 is closed by a plate 62. The vent pipe means also includes a vent pipe section 63 connected to the cylindrical member 61 and opens into the cylindrical member 61. The vent pipe section 63 is connected to another vent pipe section 64 which extends downwardly at right angles to the horizontal vent pipe section 63. The vent pipe section 64 is of such a length so its lower extremity is generally flush with the lower extremity of the Dewar flask 11.

Means is provided for recirculating cryogenic liquids which may boil off in the trap and consists of a pipe 66 which has one end threaded into the trap of the pump 66 and which has the other end connected to the vertical sleeve 39. Thus, it can be seen that any of the cryogenic liquid which is boiled off is returned through the pipe 66 to the sleeve 39 and is reintroduced into the chamber 23 so that it is not wasted.

A level sensing assembly 71 is mounted on the Dewar flask 11. It consists of a cylindrical sleeve 72 which is mounted in the top walls 16 and 19 and which is provided with a flange 73. A flange 74 is mounted on the flange 73 and is secured thereto by cap screws 76. The flange 74 carries a pair of fittings 77 which form a vacuum-tight seal with respect to the flange 74. The fittings 77 carry probe means and first and second thermocouple assemblies 78 and 79 which form lower and upper probes respectively. The thermocouple assemblies 78 and 79 carry heating means in the form of resistors 81 and 82, respectively on the lower extremities thereof. As will be noted from FIG. 2, one of the thermocouple assemblies 79 is substantially shorter than the other thermocouple assembly 78 for a reason hereinafter described. Generally, the thermocouple assemblies 78 and 79 have such a length os that the heating means 81 and 82 carried thereby are generally disposed at two separate levels within the chamber 23 with one of the levels representing the predetermined or desired low level for the liquid 83 as represented by the line 84 being sensed by the resistor 81 and the associated thermocouple assembly carried by the thermocouple assembly 78 and the high level mark for the liquid 83 as represented by the mark 86 being sensed by resistor 82 and the associated thermocouple assembly.

The thermocouple assemblies 78 and 79 are provided with additional fittings 88 which carry a plate 89 that has a connector 91 mounted thereon. The connector 91 is provided with two pins 92 and 93 in which pin 92 is connected to ground as represented by the plate 89 and pin 93 is connected to a wire 94 which extends through a sleeve 96 mounted in the flange 74. The wire 94 is provided with an expansion loop 97 within the sleeve 72 and is connected to the resistor 82. Another wire 98 connects the wire 94 to the resistor 81. The connector 91 is connected to another connector 99 which is connected by a cable 101 to a source of power. Connectors 102 and 103 are mounted on the thermocouple assemblies 78 and 79 and are connected to connectors 104 and 106 respectively. The connectors 104 and 106 are connected by cables 107 and 108 to circuitry hereinafter described.

The level sensing assembly 71 is connected to a control cabinet (not shown) which contains the circuitry which is shown in FIG. 3.

Baffle means 111 is provided in the chamber 23 for surrounding the thermocouples and consists of a baffle plate 112 which is generally V-shaped in cross-section as shown in FIG. 1 and which has outer toe portions 112a that are secured to the inner surface of the side wall 18 by suitable means such as spot welding. The baffle plate 112 extends the length of the inner chamber 23 (see FIG. 2). Half-moon shaped openings 113 are formed in the upper and lower extremities of the baffle plate 112. The lower half-moon shaped openings 113 in the baffle provide the only access for the liquid within the flask 11 to reach the thermocouples 78 and 79, whereas the upper half-moon shaped openings 113 serve as the only escape for generated gases. As hereinafter explained, the purpose of the baffle means 111 is to minimize as mush as possible the turbulence of the liquid in the vicinity of the thermocouples and thereby prevents erratic heating and cooling of the resistors 81 and 82 which could give false level indications.

Operation of the level control apparatus and method for cryogenic liquids may now be briefly described as follows in connection with the circuitry which is shown in FIG. 3 and which is normally mounted in a control box or boxes as represented by the equipment or apparatus which is enclosed within the broken line boxes or rectangles 116 and 117 shown in FIG. 3.

By way of example, the thermocouples can be of the Thermoelectric No. 41401 type. The solenoid identified as SOL for the solenoid operated valve 33 can be a VAlcor No. 90C89C-7A. A meter relay identified as MB1 is provided within the box 116. The meter relay MB1 is a Model API with a double set point and is provided with a scale 121 and a needle 122. Two set point indicators 123 and 124 are provided in which the indicator 123 is the lower set point indicator and the indicator 124 is the upper set point indicator. Contacts 5, 6 and 7, and movable arm 8 are associated with the upper set point indicator 124 and the set of contacts 1, 2, 3, and movable arm 4 are associated with the lower set point indicator 123. In addition, in the box 116, a transformer T1 is provided for reducing the voltage from 115 volts to the desired voltage as, for example, 28 volts. A lamp L is provided to give an indication when the transformer is energized. A relay K1 is provided and has two sets of contacts K1A and K1B.

In box 117, switch SW1 and pushbutton PB1 are provided in which SW1 is for the application of power and PB1 is provided for silencing the alarm. A red lamp is provided for giving an indication when the source of cryogenic liquid is empty and the white light W is provided to give an indication when the flask is being filled. A timer TD-1 has a set of contacts TD-1A. A buzzer BU is provided for giving an audible alarm.

In connection with the description of the operation of the level control apparatus and the method utilized in connection therewith, it should be appreciated that the thermocouple assemblies are sources of EMF and that a thermocouple normally generates a potential of one polarity above room temperature but when the thermocouple is cooled below room temperature, the polority reverses.

Let it be assumed that the liquid level in the chamber 23 is at a level between the lower limit represented by the line 84 and the upper limit represented by the line 86 as, for example, a mid-point as represented by the line 126. When this is the case, the indicating needle 122 of the meter relay MR1 is between the set points 123 and 124. The relay K1 is not energized which means that its contacts K1B are opened and, therefore, no energy is being supplied to the solenoid SOL and, therefore, the solenoid valve 33 is closed.

As the cryogenic liquid is utilized, the level falls within the chamber 23. The resistors 81 and 82 have a suitable value as, for example, 100 ohms. As the level continues to drop within the chamber 23 to the level represented by line 84, the liquid applies less and less cooling to the resistor 81 so that the thermocouple 78 is heated up and a potential is applied to the meter relay MR1 causing needle 122 to cross set point 124, which causes arm 8 to move over to contact 5 and energizes the relay K1 from the 115 VAC supply through contact 3, arm 4, contact 2, contact 7, arm 8 and contact 5 through relay K1 to ground. As soon as relay K1 is energized, contacts K1B are closed which energizes the solenoid SOL that operates the solenoid operated valve 33 to open the same to permit the cryogenic liquid to enter the chamber 23 through the inlet tube 29. At the same time that the contacts K1B are closed, the contacts K1A are closed to established a self-locking circuit for maintaining energization of the relay K1.

As soon as the cryogenic liquid as, for example, liquid nitrogen, enters the chamber 23, the level of the liquid will rise above the level 84 and the resistor 81 for the thermocouple 78 will agian be covered and become cold to cause the meter relay MR1 needle 122 to cross set point 124 and cause arm 8 to move from the contact 5 to contact 6. However, relay K1 is not deenergized because it is held in an energized position by the hold or lock-up circuit formed by the relay contacts K1A. Thus, once the relay K1 is energized, it remains energized as does the solenoid SOL.

Therefore, cryogenic liquid continues to flow into the chamber 23 and the level continues to rise until the upper resistor 82 is cooled by the cryogenic liquid. When the cryogenic liquid has reached a certain level as, for example, the level 86 within the container 23, this causes a deflection of the needle 82 to the left as viewed in FIG. 3. This continues until the lower set point indicator 123 is reached, at which time the meter relay MR1 causes its movable arm 4 to move from contact 3 to contact 1 to open the circuit which energizes the relay K1. This causes deenergization of the relay K1 to open its contacts K1A and K1B which, in turn, causes deenergization of the solenoid SOL to stop the fill cycle. The movable arm 4 switches from contact 1 to contact 3 as soon as the liquid level has dropped sufficiently to permit the resistor 82 to become hot and the arm 4 will remain in this position until the end of a fill cycle is again reached as hereinbefore explained.

During most of the time, the needle 122 is relatively stationary between the upper and lower set points. The needle begins to move to the right after the resistor 81 is cleared of cryogenic liquid and starts becoming hot and heating up the thermocouple 78. As soon as the needle crosses the set point represented by the indicator 124, the connection is made between contacts 7 and 5 which cause energization of relay K1 as hereinbefore described. As soon as the cryogenic liquid flows into the chamber and re-immerses the resistor 81, the needle 122 swings to the left. It crosses the set point represented by the set point indicator 124 but does nothing because the opening of the connection between contacts 7 and 5 has no effect on relay K1. The needle 122 then returns to approximately mid-point position and remains there during the remainder of the fill cycle. When the upper resistor 82 of the thermocouple 79 forming the upper probe starts becoming cold, the needle 122 swings to the left. When it crosses the set point represented by the set point indicator 123, the connection between contacts 2 and 3 opened to deenergize the relay K1 and the solenoid SOL. Both of the probes or thermocouples 78 and 79 are now cold and the needle 122 remains in the left position or at a −4.

As the cryogenic liquid is utilized, the chamber 23 and the resistor 82 are uncovered, the upper probe or thermocouple 79 will again become hot and the needle 122 will swing to the right and will come to a rest position at minus 1½ which is a condition represented by one probe being hot and one probe being cold.

In connection with the present apparatus, it should be appreciated that there is a certain amount of coasting because it takes time to cool off a probe or to heat a probe to the desired temperature so that the level is still changing while this is occurring. Switching action by the meter relay MR1 takes place when the indicating needle which measures the thermocouple voltage crosses either the upper or lower set points. The visual display provided by the meter relay MR1 is not required but it does provide a visual check on the operation of the apparatus.

The visual display provided by the light R and W and the audible alarm provided by the buzzer BU are provided to give indications to the operator so that when the source of cryogenic liquid has been exhausted, he must take steps to replace the source. Thus, for example, if liquid nitrogen is being utilized and kept in bottles, this permits the operator to change bottles of liquid nitrogen. With the present arrangement, there are approximately 4 minutes provided for such a purpose. If the liquid nitrogen is not supplied from the source within a predetermined time as, for example, 4 minutes, the timer TD-1 will time out to close its contacts TD-1A, and will give such an indication by the buzzer BU and the red light R. The buzzer BU and the red light can be turned off by operating the pushbutton PB2. Thus, the pushbutton PB2 serves as a silencing pushbutton and, in addition, it serves as a reset pushbutton.

The light W is a white light and is lit when the trap is being filled with the cryogenic liquid. The switch SW1 is provided for turning power on to the apparatus and a white light W is provided to give an indication when the apparatus has its power turned on.

It is apparent from the foregoing that there has been provided a level control apparatus and method for cryogenic liquids which is particularly useful in connection with vaccum equipment as, for example, vacuum chambers which are utilized for coating operations. During a major portion of the time as, for example, 95% of the time, the level control apparatus remains in a condition in which one of the thermocouples or probes is hot and the other is cold. By way of example, when a thermocouple is heated, it puts out approximately 8 millivolts in its normal polarity, whereas when it is cooled with a cryogenic liquid it puts out 8 millivolts in reverse polarity. In the situation in which the liquid level is between the two thermocouples, the outputs cancel each other. When both of them are hot, they are additive in one direction and when both of them are cold, they are additive in the opposite direction.

As the cryogenic liquid is being introduced into the chamber 23 through the inlet pipe 29, it is diffused by the diffuser assembly 42. The V-shaped diffuser plate 44 serves to prevent turbulence and atomizing of the liquid to thereby minimize boil-off. The cryogenic liquid will tend to take a downward path and rebound off of the wall of the second container 13 and be directed downwardly toward the liquid in the tank to thereby inhibit undue boil-off with its inherent waste of the cryogenic liquid.

To improve the accuracy of the level control apparatus, the baffle plate 112 has been provided which completely encloses the thermocouple assemblies or probes 78 and 79. The only entrance for the liquid so that it can come in contact with the thermocouples is through the half-moon holes 113 provided in the baffle 112 at the bottom of the second container 13. Any gas which is generated must exit through the half-moon openings 113 provided at the top of the baffle 112 and the second container 13. The baffle 112 serves to prevent any sporadic change in the liquid level or turbulence in the main chamber from substantially affecting the capability of the thermocouples for accurately sensing thhe level of the liquid in the chamber 23. This serves to prevent erratic operation of the thermocouples.

The cryogenic liquid is maintained at a level in the Dewar flask or vessel 11 so that there is always an adequate supply for the trap of the pump 56. As pointed out previously, the trap of the pump can be vented to the Dewar itself or to the pipe 66 so that any boil-off occurring within the trap can either bubble up into the liquid level within the Dewar flask 11 by coming up through the inner tubular member 46, or alternatively, a separate pipe can be provided which is connected into the trap and vented into the pipe 66 in the sleeve 39 so that it will be introduced into the Dewar flask.

With the arrangement shown, the entry of water into the Dewar flask is minimized while still providing adequate venting. As long as there is a cryogenic liquid present in the trap or in the Dewar flask, there will always be a certain amount of gas present in the Dewar flask which will create a positive pressure inside the Dewar flask. When this is the case, no air will enter the Dewar flask and, therefore, consequently no condensation will form and water droplets cannot enter the Dewar flask as long as there is such a positive pressure.

It is apparent from the foregoing that the level control apparatus of the present invention has a number of outstanding advantages. One of the principal advantages is that it has a relatively simple construction so that it is practically maintenance-free. Since the filling cycle is very reliable, there is no spillage from overfilling. In addition, boil-off from the Dewar flask itself is minimized because of the evacuation provided for the Dewar flask and also because of the internal shielding provided by the layers 26. By way of example, it has been found that the use of a level control apparatus of the present type in conjunction with vacuum type coating equipment results in savings as high as 50% in the amount of liquid nitrogen consumed in a particular coating machine.

Because of the baffling provided, the liquid level sensors can sense the liquid level quite readily and, therefore, ensure that filling of the Dewar flask will occur at the proper times and that overfilling will not occur.

Considerable effort has been utilized in the fabrication of the Dewar flask to ensure reliability. There are no mechanical joints which can come loose. All the joints have been heliarc welded. All leads have been silver soldered in place. Leads have been provided with shock loops to accommodate any expansion or contraction which occurs. In addition, it can be seen that the resistors 81, 82 are directly silvered to the bottom of the thermocouple or probe to obtain better conduction from the resistor and the thermocouple. This also makes possible faster response times.

It is very important for operation of the solenoid that air which could contain moisture does not come in contact with the solenoid. Such moisture could condense out and cause the valve to freeze up and impair its operation. Thus, by ensuring that the cryogenic liquid always will be present in the Dewar flask, a positive pressure will be present in the flask to prevent air from entering the flask.

It should be appreciated that, if desired, a single thermocouple and heating means can be utilized for such a purpose. However, this has a disadvantage in that the liquid level could vary a small amount before the thermocouple would create a change in voltage output which, in turn, could be utilized for energizing a solenoid to cause filling of the chamber. This would necessitate filling at very frequent intervals with consequent cycling of the solenoid and could radically decrease its lifetime. With the arrangement disclosed in the drawings in which two thermocouples and two heating means are provided with such thermocouples, the cycle time can easily range from 15 to 20 minutes with a consequent substantially lesser wear and tear on the solenoid which should mean that the solenoid and the level control apparatus should be relatively trouble-free for a period of 3 or 4 years or greater.

We claim:

1. In a level control apparatus for a cryogenic liquid, a source of cryogenic liquid, an insulated flask having a chamber for holding a cryogenic liquid, inlet means mounted on the flask for introducing a cryogenic liquid into the chamber, outlet means mounted on the flask for permitting cryogenic liquid to be removed from the flask, first and second probe assemblies mounted in the flask and having their lower extremities at different elevations within the chamber which are adapted to be covered by the cryogenic liquid within the chamber, each of said probe means including thermocouple means for generating a voltage in response to temperature and heating means for generating heat and supplying the same to the thermocouple means whereby the thermocouple means produces a signal of one type when the heating means is in contact with the cryogenic liquid and a signal of a different type when at least a portion of the heating means is out of contact with the cryogenic liquid, and means responsive to the signals from said thermocouple means of the first and second probe assemblies for automatically controlling the flow of cryogenic liquid from said source into said inlet means, said means responsive to the signals from said thermocouple means in said first and second probe assemblies including a meter relay having upper and lower set points corresponding to two temperatures, one hot and one cold, with the hot temperature being reached when the heating means for both of said first and second probe assemblies are no longer covered by the cryogenic liquid and with the cold temperature being reached when the heating means for both of said first and second probe assemblies are substantially covered by said cryogenic liquid, solenoid operated valve means connected between the source and the inlet for controlling the flow of cryogenic liquid from said source to said inlet and relay means responsive to the meter relay for controlling operation of said solenoid operated valve means whereby filling of chamber with cryogenic liquid from said source is started when the upper set point is reached and continues until the lower set point is reached.

2. Level control apparatus as in claim 1 together with alarm means and means for actuating said alarm means within a predetermined period of time after the upper set point is reached and no cryogenic liquid has entered the chamber.

3. Level control apparatus as in claim 1 wherein said heating means is in the form of a resistor directly connected to the thermocouple means.

4. Level control apparatus as in claim 1 together with baffle means for protecting said heating means from turbulence and wave motion of the cryogenic liquid in the chamber.

5. Level control apparatus as in claim 4 wherein said baffle means comprises a member extending the height of said chamber and surrounding said probes, said baffle means having relatively small openings therein so that the cryogenic liquid in the vicinity of the probes is maintained relatively free of erratic movement of the cryogenic liquid.

6. Level control apparatus as in claim 1 wherein said inlet means includes an inlet pipe, a diffuser assembly mounted on the inlet pipe and diffusing the cryogenic liquid outwardly and downwardly against the side walls of the Dewar flask.

7. Level control apparatus as in claim 1 wherein said flask is in the form of first and second containers with an evacuated space therebetween and foil means disposed in said space.

* * * * *